(12) United States Patent
Schaffer et al.

(10) Patent No.: US 8,798,937 B2
(45) Date of Patent: Aug. 5, 2014

(54) METHODS FOR OPTIMIZING AND USING MEDICAL DIAGNOSTIC CLASSIFIERS BASED ON GENETIC ALGORITHMS

(75) Inventors: J. David Schaffer, Wappingers Falls, NY (US); Mark R. Siimpson, Wappingers Falls, NY (US)

(73) Assignee: Koninklijke Philips N.V., Eindhoven (NL)

( * ) Notice: Subject to any disclaimer, the term of this patent is extended or adjusted under 35 U.S.C. 154(b) by 2160 days.

(21) Appl. No.: 10/597,767

(22) PCT Filed: Feb. 1, 2005

(86) PCT No.: PCT/IB2005/050426
§ 371 (c)(1), (2), (4) Date: Aug. 7, 2006

(87) PCT Pub. No.: WO2005/078629
PCT Pub. Date: Aug. 25, 2005

(65) Prior Publication Data
US 2007/0172828 A1    Jul. 26, 2007

Related U.S. Application Data

(60) Provisional application No. 60/543,461, filed on Feb. 10, 2004, provisional application No. 60/639,747, filed on Dec. 28, 2004.

(51) Int. Cl.
*G01N 33/48* (2006.01)
*G06F 19/24* (2011.01)

(52) U.S. Cl.
CPC .................................. *G06F 19/24* (2013.01)
USPC ........................................................ 702/20

(58) Field of Classification Search
None
See application file for complete search history.

(56) References Cited

U.S. PATENT DOCUMENTS

| | | |
|---|---|---|
| 6,260,031 B1 | 7/2001 | Schaffer et al. |
| 6,553,357 B2 | 4/2003 | Mathias et al. |
| 2004/0058340 A1 | 3/2004 | Dai et al. |

FOREIGN PATENT DOCUMENTS

| | | |
|---|---|---|
| EP | 1 296 281 A2 | 3/2003 |
| WO | 0199043 A1 | 12/2001 |

OTHER PUBLICATIONS

Ooi et al. (Bioinformatics, 2003, vol. 19, No. 1, p. 37-44).*
Liu et al. (Evolutionary Computation, 2002, May 12-17, 2002, pp. 297-302).*
Vogt et al. (Clin. Chem., 1992, 38/2, 182-196).*
Booker et al. (Artificial Intelligence, 1989, 40, 235-282).*
Dybowski et al. (Lancet, 1996, 347, 1146-50).*
Au, W., et al.; A Novel Evolutionary Data Mining Algorithm with Applications to Churn Prediction; 2003; IEEE Trans. on Evolutionary Computation; 7(6)532-544.
Bandyopadhyay, S., et al.; Incorporating Chromosome Differentiation in Genetic Algorithms; 1998; Information Sciences; 104:293-319.
Chtioui, Y., et al.; Feature Selection by a Genetic Algorithm. Application to Seed Discrimination by Artificial Vision; 1998; J. Sci.Food Agric.; 76:77-86.
Lemmon, A.R., et al.; The metapopulation genetic algorithm: An efficient solution for the problem of large phylogeny estimation; 2002; PNAS; 99(16)10516-10521.
Brazma, A., et al.; A quick introduction to elements of biology-cells, molecules, genes, functional genomics, microarrays; 2004; http://www.evi.ac.uk/microarray/biology_intro.html.
Eshelman, L.J.; The CHC adaptive search algorithm: How to Have Safe Search When Engaging in Nontraditional Genetic Recombination; 1991; San Francisco, CA; pp. 265-283.
Mathias, K. E., et al.; Code Compaction Using Genetic Algorithms; 2000; San Francisco, CA; pp. 710-717.
Petricoin, E. F., et al.; Use of Proteomic Patterns in Serum to Identify Ovarian Cancer; 2002; Lancet; 359:572-577.
Van'T Veer, L. J., et al.; Gene Expression Profiling Predicts Clinical Outcome of Breast Cancer; 2002; Nature; 415:530-536.
Whitley, D.; A Genetic Algorithm Tutorial; 1994; Statistics and Computing; 4:65-85.
Quinlan, J.R.; Induction of Decision Trees; 1986; Machine Learning; vol. 1, pp. 81-106.
Reddy, A.R., et al.; Identification of Multiple Gene Subsets Using Multi-objective Evolutionary Algorithms; 2003; LNCS; 2632; pp. 623-637.
Rosskopf, M., et al.; Classification of Leukemia Classes by GP-based DNA-Chip Analysis; 2003; BioGen Workshop GECCO; pp. 81-82.
Ooi, C.H. et al "Genetic Algorithms Applied to Multi-Class Prediction for the Analysis of Gene Expression Data", BIOINFORMATICS, vol. 19, No. 1, 2003, pp. 37-44.

* cited by examiner

*Primary Examiner* — Pablo S Whaley

(57) ABSTRACT

In a genetic optimization method, the genes of a chromosome population are computationally genetically evolved. The evolving includes evolving a number of expressed genes in each chromosome and employing a fitness criterion evaluated without reference to unexpressed genes of each chromosome. An optimized chromosome produced by the genetic evolving is selected.

17 Claims, 6 Drawing Sheets

Figure 1:
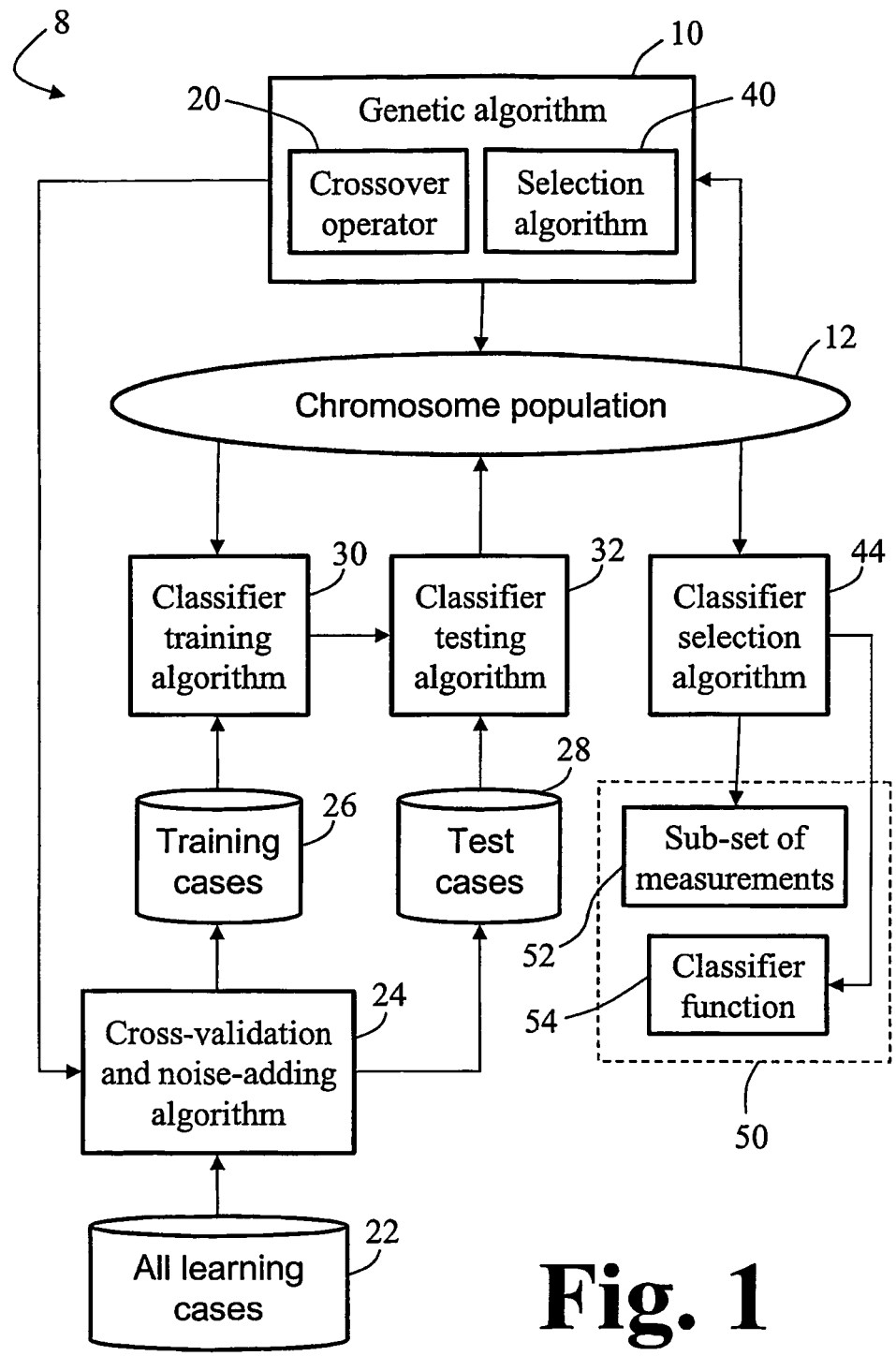

METHODS FOR OPTIMIZING AND USING MEDICAL DIAGNOSTIC CLASSIFIERS BASED ON GENETIC ALGORITHMS

CROSS REFERENCE TO RELATED APPLICATIONS

This application claims the benefit of U.S. provisional application Ser. No. 60/543,461 filed Feb. 10, 2004 and U.S. provisional application Ser. No. 60/639,747 filed Dec. 28, 2004, both of which are incorporated herein by reference.

The following relates to the genetic algorithms. It finds particular application in genomics-based medical diagnostic tests, and will be described with particular reference thereto. More generally, it finds application in optimization of classifiers for bioinformatics and other applications, in software code compaction, in development of neural networks, and so forth.

There has recently been an enormous explosion in the amount of available information on the details of the human genome and how the genes are expressed in healthy and diseased subjects. Laboratory techniques are now available to rapidly acquire large sets of measurements characterizing concentrations of DNA, RNA, proteins, and other organic macromolecules in a biological subject.

Microarrays, for example, include glass slides or plates on which arrays of small sample "dots" of c-DNA or another binder are disposed. Each dot includes a specific c-DNA or other binder that bonds with a specific macromolecule of interest, and a single microarray may include hundreds, thousands, or more such dots. A tissue sample is extracted from a patient, and the molecular species of interest (for example, DNA, RNA, or so forth) is extracted and treated with a luminescent signaling agent or other marker, and washed over the microarray. Specific types of macromolecules in the tissue collect at dots having binders keyed to those specific macromolecules in a process called hybridization. Typically, a comparison or reference sample treated with a different marker (for example, a differently colored luminescent agent) is also applied to the microarray. The marker or markers are excited, for example using a laser beam to produce photoluminescence, and the response intensity is measured to characterize the concentration of macromolecules associated with the various dots. In this way, an assay of a large number of organic macromolecules (e.g., hundreds, thousands, or more) contained in the biological sample is rapidly and quantitatively performed.

Mass spectrogram analysis is another method for rapidly assaying concentrations of large numbers of macromolecules in a sample drawn from a patient. In this approach, the sample is ionized by a laser or other mechanism in a vacuum environment, and the distribution of molecular weight/electric charge ratios of the ionized molecular fragments is measured by an ion counter. Based on known cracking patterns for various macromolecules, the concentrations of various macromolecules can be derived from the mass spectrogram. Alternatively, the peaks of the mass spectrogram can be used as bioinformatic measurement data without correlating the mass spectrogram pattern with specific macromolecules.

Bioinformatics employs numerical methods to extract useful biological information from microarray measurements, mass spectrograms, or other genomic or organic macromolecular assays. For example, if a particular pattern in the microarray or mass spectrogram can be strongly correlated with a particular type of cancer, then the pattern can be used as a classifier for screening for that cancer. This enables early detection of cancers and other pathologies of interest using relatively non-invasive techniques such as drawing blood or cerebral spinal fluid, taking a sample of saliva, urine, feces, or so forth, or otherwise acquiring a fluid or tissue sample.

A problem arises, however, due to the large quantity of information available for developing such diagnostic medical tests. For example, if it is desired to develop a cancer screening test employing five measurements (such as microarray dots, mass spectrogram peaks, or so forth) out of a set of 2500 measurements (such as a microarray with a 50×50 array of dots), then the search space of possible five-sample measurement sub-sets that can be used for the diagnostic test is:

$$\binom{2500}{5} = \frac{2500!}{2495! \cdot 5!} \cong 8.1 \times 10^{14}, \qquad (1)$$

which is far too large to be searched using an exhaustion technique. Moreover, the estimate of Equation (1) assumes that a sub-set of five measurements is optimal for the cancer screening test under development, which may be incorrect. The optimal sub-set of measurements may be four measurements, six measurements, or so forth and is usually unknown.

Another problem in developing genomic diagnostic medical tests is that although the total number of measurements is large, the pool of patients from which these measurements are drawn is typically much smaller. For example, a typical study may use a 50×50 microarray and a test group of 40 test subjects in which 20 subjects have the cancer of interest and 20 subjects are controls who do not have the cancer. A large set of 100,000 measurements is generated; however, the small 40 test subject group size raises the concern that there may be many false correlations in the measurement data that do not relate to the cancer of interest in the general population.

Genetic algorithms have been used in such optimization problems. In genetic algorithms, an initial generation chromosome population is produced, in which each chromosome has a set of genes that indicates a sub-set of the set of measurements. For example, using a set of measurements generated by a 50×50 microarray, each gene has a value between 1 and 2500 corresponding to the 2500 measurements provided by the 2500 dots of the microarray. Five such genes in a single chromosome suitably specifies a specific sub-set of five of the 2500 measurements. A classifier is optimized for each chromosome. The classifier uses the sub-set of genes specified by the chromosome to classify subjects into two or more classifications (for example, a cancer classification and a non-cancer classification). A figure of merit measures how accurately the classifier identifies cancer in a group of patients, and is used to select the most fit chromosomes of the chromosome pool for propagation into future generations. Further, offspring chromosomes are mutated by random or pseudorandom changes in the gene values analogously to biological mutation processes.

While based on biological evolution concepts, genetic algorithms typically deviate from biological evolutionary processes in various ways. An overview of some genetic algorithms is provided in Whitley, "A Genetic Algorithm Tutorial", Statistics and Computing vol. 4 pages 65-85 (1994). One robust genetic algorithm is the cross-generational elitist selection, heterogeneous recombination, cataclysmic mutation (CHC) algorithm developed by Larry Eshelman. The Eshelman CHC algorithm or variants thereof are disclosed, for example, in: Schaffer et al., U.S. Pat. No. 6,260,031 issued Jul. 10, 2001; Mathias et al., U.S. Pat. No. 6,553,357 issued Apr. 22, 2003; and Eshelman, "The CHC Adaptive Search Algorithm: How to Have Safe Search When Engaging in Nontraditional Genetic Recombination", Foundation of Genetic Algorithms, Gregory Rawlins (ed.), Morgan Kaufmann, San Francisco, Calif., 265-83 (1991). Genetic algorithms have been found to efficiently search large spaces, and as such are well-suited for identifying small measurement sub-sets from genomic assays such as microarrays and mass spectrograms for use in diagnostic medical testing.

However, existing genetic algorithms have certain disadvantages for bioinformatics and other applications. In optimizing classifiers using genetic algorithms, the genetic algorithm must be re-executed for each sub-set size under investigation. Thus, for example, five independent computational genetic evolution runs are performed to span sub-set sizes of three to seven measurements. Moreover, mutation rates typically are low, for example around a one percent or lower, so as to ensure sufficient cross-generational continuity to provide meaningful convergences. However, low mutation rates slow down the overall discovery rate.

Still further, in bioinformatics applications the set of measurements is typically sample-rich but subject-poor (e.g., 2500 measurements applied to a pool of only 40 human test subjects). Such subject-poor data sets lead to the possibility of convergence to false correlations that are not highly predictive of the pathology of interest in the general population.

The following contemplates improved apparatuses and methods that overcome the aforementioned limitations and others.

According to one aspect, a method is provided for determining a classifier. A first generation chromosome population of chromosomes is produced. Each chromosome has (i) a selected number of genes specifying a sub-set of an associated set of measurements and (ii) an expressed sub-set-size gene having a value distinguishing expressed and unexpressed genes of the chromosome. The genes of the chromosomes including the expressed sub-set-size gene are computationally genetically evolved respective to a fitness criterion evaluated without reference to unexpressed genes to produce successive generation chromosome populations. A classifier is selected that uses the sub-set of associated measurements specified by the expressed genes of a chromosome identified by the genetic evolving.

According to another aspect, a method is provided for determining a classifier. A first generation chromosome population of chromosomes is produced. Each chromosome has a selected number of genes specifying a sub-set of an associated set of measurements. The genes of the chromosomes are computationally genetically evolved to produce successive generation chromosome populations. The producing of each successor generation chromosome population includes: generating offspring chromosomes from parent chromosomes of the present chromosome population by: (i) filling genes of the offspring chromosome with gene values common to both parent chromosomes and (ii) filling remaining genes with gene values that are unique to one or the other of the parent chromosomes; selectively mutating genes values of the offspring chromosomes that are unique to one or the other of the parent chromosomes without mutating gene values of the offspring chromosomes that are common to both parent chromosomes; and updating the chromosome population with offspring chromosomes based on a fitness of each chromosome determined using the sub-set of associated measurements specified by genes of that chromosome. A classifier is selected that uses the sub-set of associated measurements specified by genes of a chromosome identified by the genetic evolving.

According to another aspect, a method is provided for determining a classifier. A first generation chromosome population of chromosomes is produced. Each chromosome has a selected number of genes specifying a sub-set of an associated set of measurements. The genes of the chromosomes are computationally genetically evolved to produce successive generation chromosome populations. The producing of each successor generation chromosome population includes: introducing a selected level of simulated noise into values of the set of measurements for a group of subjects; generating offspring chromosomes by mating chromosomes of the present chromosome population; selectively mutating genes of the offspring chromosomes; and updating the chromosome population with offspring chromosomes based on a fitness of each chromosome determined respective to the values of the measurements of the group of subjects with the introduced simulated noise. A classifier is selected that uses the sub-set of associated measurements specified by genes of a chromosome identified by the genetic evolving.

According to another aspect, a medical diagnostic test is disclosed for determining whether a medical subject has a pathology of interest. Measurements of the medical subject are classified using a medical diagnostic classifier determined by one of the methods of the preceding three paragraphs, wherein the associated set of measurements characterize concentrations of organic macromolecules.

According to another aspect, a genetic optimization method is provided. The genes of a chromosome population are computationally genetically evolved. The evolving includes evolving a number of expressed genes in each chromosome and employing a fitness criterion evaluated without reference to unexpressed genes of each chromosome. An optimized chromosome produced by the genetic evolving is selected.

One advantage resides in optimizing a classifier for a bioinformatic or other application without requiring a priori knowledge or selection of the number of measurements to be incorporated into the classifier.

Another advantage resides in providing more robust convergence in genetic evolutionary based optimizations.

Another advantage resides in providing a robust convergence in combination with a high mutation rate.

Yet another advantage resides in reduced sensitivity of genetic algorithm convergence to systematic errors in the set of measurements.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

FIG. 1 diagrammatically shows an optimization system using a genetic algorithm.

Figure 2:
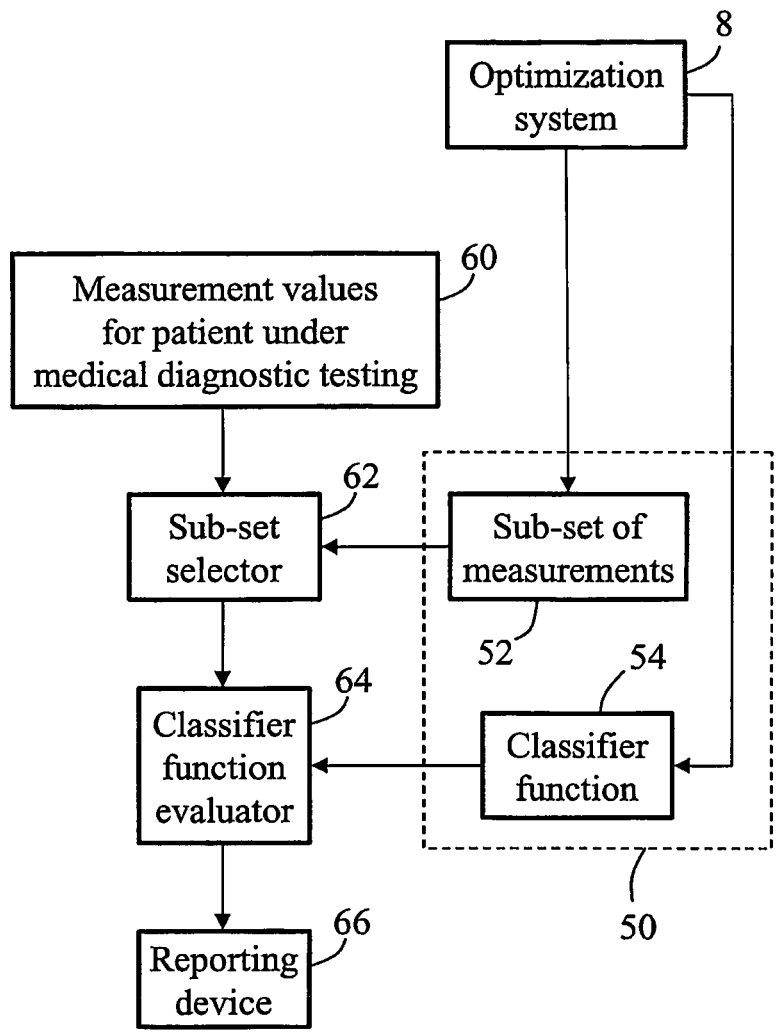

FIG. 2 diagrammatically shows an implementation of a diagnostic medical test developed using the optimization system of FIG. 1.

Figure 3A:
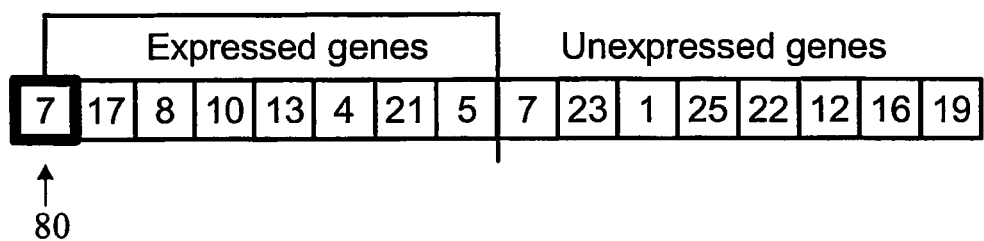
Figure 3B:
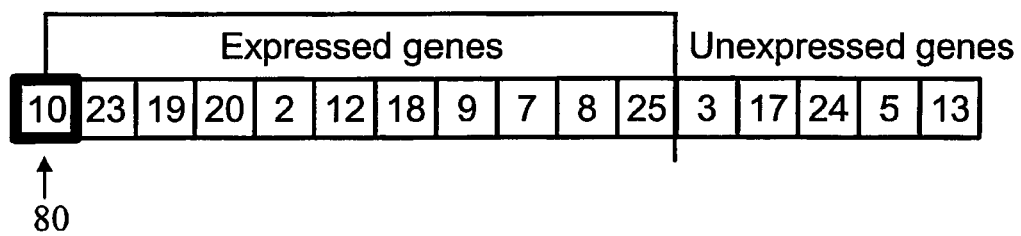

FIGS. 3A and 3B diagrammatically show two example chromosomes each with sixteen genes including an expressed sub-set-size gene and other genes whose values identify measurements that may be used in a classifier. The chromosome of FIG. 3A has seven expressed measurement genes, while the chromosome of FIG. 3B has ten expressed measurement genes.

FIGS. 4A, 4B, 4C, and 4D diagrammatically show operation of the crossover operator of FIG. 1 operating on the two example chromosomes of FIGS. 3A and 3B to produce two offspring chromosomes.

Figure 5:
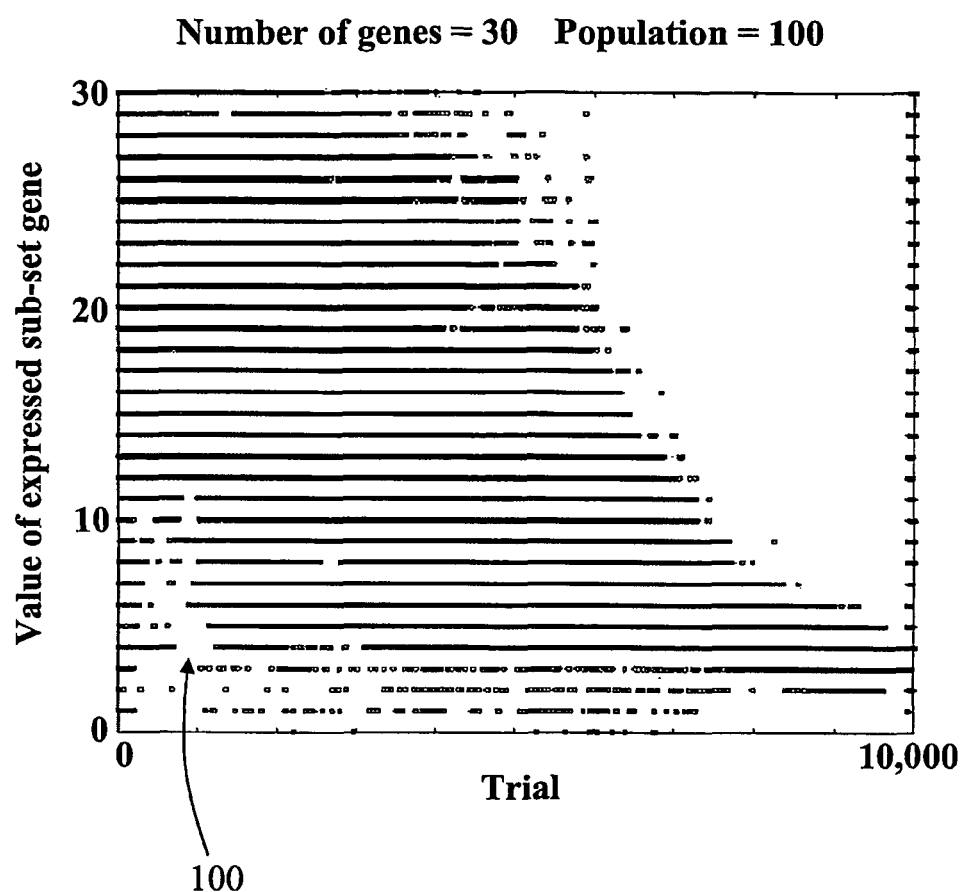

FIG. 5 shows a scatter plot of a computational genetic evolution optimization performed using the system of FIG. 1. In FIG. 5, the value of the expressed sub-set-size gene of each chromosome is plotted along the ordinate (y-axis) and the trial number (corresponding to time) is plotted along the abscissa (x-axis).

With reference to FIG. 1, an optimization system 8 includes a genetic algorithm 10 operating on a chromosome population 12. For the example optimization of a bioinformatics classifier, each chromosome typically includes a plurality of genes, in which the value of each gene specifies a particular biological measurement. For example, if the biological measurements are performed as 100×100 dot microarrays acquired from a set of test subjects, then there are 10,000 dots per microarray, that is, 10,000 measurements. Each gene suitably contains an index value (for example, an integer ranging between 1 and 10,000 inclusive, or between 0 and 9,999 inclusive, or so forth) which indexes a measurement. The first generation chromosome population is suitably generated by randomly or pseudorandomly assigning each gene a value within the index range, usually insuring that no index is duplicated. Alternatively, the assignments may be less than wholly random—for example, the assignments may be biased toward certain groups of genes that are suspected of being effective for the classifier to be optimized.

To generate a next generation chromosome population, a crossover algorithm 20 combines parent chromosomes of the present generation population using suitable operations such as gene copying, gene mixing, gene mutation, and so forth to produce offspring chromosomes. The present generation chromosomes and the offspring chromosomes are characterized by a figure of merit to determine the fitness or survivability of each chromosome. In the bioinformatics classifier optimization illustrated in FIG. 1, optimization is performed with respect to a set of learning cases 22 which are divided by a cross-validation and noise-adding algorithm 24 into a sub-set of training cases 26 and a sub-set of test cases 28. The cross-validation division is typically performed before each new generation chromosome population is evaluated.

For each chromosome, the classifier is optimized with respect to the training cases 26 by a classifier training algorithm 30. For example, the classifier may be a weighted sum of the measurement values of the sub-set of measurements selected by the expressed genes of the chromosome, and the optimization may involve optimizing the weighting factors. More complex classifiers can be also employed. In some bioinformatics classification applications, the learning cases 22 are a pool of human test subjects, some of whom have a pathology of interest (for example, a specific type of cancer) and others of whom do not have the pathology of interest. The classifier defined by the sub-set of measurements specified by a chromosome is optimized such that the classifier maximizes its ability to sort the learning cases 22 into a first classification of individuals having the pathology of interest and a second classification of individuals who do not have the pathology.

Once the classifier for a chromosome is optimized, a classifier testing algorithm 32 tests how effective the optimized classifier is at classifying the individuals of the test cases 28 into the first classification of individuals having the pathology of interest and the second classification of individuals who do not have the pathology. A suitable figure of merit quantifying the fitness or survivability of the chromosome is, for example, a count of the number of erroneous classifications made by the optimized classifier, or a ratio of the number of erroneous classifications of test case subjects to the total number of individuals in the test cases 28.

The processing performed by the classifier training algorithm 30 and the classifier testing algorithm 32 is repeated for each chromosome so the chromosomes of the chromosome population 12 are assigned figures of merit for fitness or survivability. A selection algorithm 40 selects which chromosomes survive to the next generation based on a suitable selection criterion or criteria. This process is repeated each successive generation to computationally genetically evolve the chromosome population 12 until the genetic algorithm 10 detects a suitable stopping criterion or criteria, such as the number of surviving offspring being less than a threshold, or the percent change in population being less than a threshold, or so forth.

A classifier selection algorithm 44 examines the final chromosome population to identify the most fit chromosome, which is used to construct a suitable diagnostic test 50 for the pathology of interest. The diagnostic test typically identifies the sub-set of measurements 52 corresponding to the expressed genes of the most fit chromosome and the optimized classifier function 52 employing the sub-set of measurements 52.

With reference to FIG. 2, the diagnostic medical test 50 is suitably applied as follows. Measurement values 60 are acquired of a patient under testing. To increase efficiency, typically only those measurements used in the diagnostic test 50 are acquired. A classifier function evaluator 64 evaluates the classifier function 54 with respect to the sub-set of measurement values to produce a positive (cancer detected) or negative (cancer-free) test result, which is reported to medical personnel by a suitable reporting device 66 (for example, a video display, a printout, or so forth).

Advantageously, it will be appreciated that once the diagnostic medical test 50 is developed as previously described with reference to FIG. 1, its implementation in a hospital, clinic, or other medical facility is straightforward. For example, the processing elements 62, 64, 66 are suitably embodied as software and hardware of a computer, and the developed diagnostic test 50 is suitably represented by data stored on a hard drive or other non-volatile storage of the computer, or stored on a hospital network, the Internet, or so forth. Once the diagnostic test 50 is developed, there is no need to include the optimization system 8 in the diagnostic test system implementation deployed at a hospital, clinic, or so forth—rather, only the identification of the sub-set of measurements 52 and the classifier function 54 is deployed.

Having given an overview of the illustrated optimization system 8 and its example application to diagnostic medical testing, a more detailed description of aspects of various embodiments of the computational genetic evolutionary optimization are described with reference to FIG. 1 and with further reference to FIGS. 3A, 3B, 4A, 4B, 4C, and 4D.

With returning reference to FIG. 1 and with further reference to FIGS. 3A and 3B, each chromosome of the chromosome population 12 has the general format shown in FIGS. 3A and 3B, where FIG. 3A diagrammatically shows one example chromosome 70 and FIG. 3B shows another example chromosome 72. Each chromosome has a fixed length of genes. In the example chromosomes 70, 72, this fixed length is sixteen genes; however, in general the chromosomes can have any selected number of genes. A selected number of genes of each chromosome are expressed, and the number of expressed genes is identified by a value of an expressed sub-set-size gene 80, which in the illustrated format is the left-most gene in an ordered set of genes running from left to right in FIGS. 3A and 3B. Each chromosome can in general have a different number of expressed genes specified by the value of its expressed sub-set-size gene 80. For example, the chromosome 70 of FIG. 3A has an expressed sub-set-size gene 80 with a value of seven, indicating seven expressed genes, while the chromosome 72 of FIG. 3B has an expressed sub-set-size gene 80 with a value of ten, indicating ten expressed genes. In the arrangement of FIGS. 3A and 3B, the expressed genes are those genes directly right of the expressed sub-set-size gene 80, and the value of the expressed sub-set-size gene 80 identifies an ordinal position value separating the expressed and unexpressed, genes of the ordered set of genes.

Thus, for example, in the chromosome 70 of FIG. 3A the value of seven in the expressed sub-set-size gene 80 identifies the seventh gene after the expressed sub-set-size gene 80 as being the last expressed gene, with those genes following the seventh gene being unexpressed genes. Similarly, in the chromosome 72 of FIG. 3B the value of ten in the expressed sub-set-size gene 80 identifies the tenth gene after the expressed sub-set-size gene 80 as being the last expressed gene, with those genes following the tenth gene being unexpressed genes. The value of the expressed sub-set-size gene 80 should in general lie between one and the maximum number of genes minus one inclusive (thus not counting the expressed sub-set-size gene 80). Thus, for chromosomes having the format of chromosomes 70, 72, the expressed sub-set-size gene 80 should have a value lying between one and fifteen. For a value of one, there is one expressed gene and fourteen unexpressed genes; for a value of fifteen there are fifteen expressed genes and no unexpressed genes. In some embodiments, this range may be limited further. For example, it may be desired that the classifier operate on no fewer than two genes—accordingly, the lower limit for the expressed sub-set-size gene would be two. Similarly, it may be desired to limit the number of expressed genes to something less than the total number of genes in the chromosome, thus assuring that there will always be one or some unexpressed genes in each chromosome.

The illustrated embodiments employ a sub-set-size gene that contains an ordinal value separating the expressed and unexpressed genes of the ordered set of genes. However, the sub-set-size gene can be embodied by other representations that distinguish expressed and unexpressed genes of the chromosome. For example, in some contemplated embodiments, the sub-set-size gene is a binary mask representation. For chromosomes with sixteen genes (not counting the sub-set-size gene) a suitable binary mask-type sub-set-size gene includes sixteen bits corresponding to the sixteen genes, with each bit having a binary value ("1" or "0") indicating whether or not the corresponding gene is expressed or unexpressed. If for example binary "1" indicates expressed while binary "0" indicates unexpressed, then the number of binary "1" values in the mask-type sub-set-size gene indicates the number of expressed genes.

Each of the genes other than the expressed sub-set-size gene 80 has a value indicating one of the measurements of a set of measurements available for possible use in the classifier. For example, if the set of measurements is obtained the learning cases 22 using 100×100 dot microarrays, each gene can suitably have a value of between 1 and 10,000 indexing the dots of the microarray. In the case of a mass spectrogram, the set of measurements may be the mass/charge ratio bins of the mass spectrogram. In the chromosome 70 of FIG. 3A, the first gene to the right of the expressed sub-set-size gene 80 has a value of 17 indexing a seventeenth measurement of the set of measurements; the second gene to the right of the expressed sub-set-size gene 80 has a value of 8 indexing an eighth measurement of the set of measurements; the third gene to the right of the expressed sub-set-size gene 80 has a value of 10 indexing a tenth measurement of the set of measurements; and so forth.

The chromosome format of FIGS. 3A and 3B is an illustrative example. The skilled artisan can readily develop other formats in which an expressed subset-size gene distinguishes expressed and unexpressed genes of each chromosome. For example, the expressed sub-set-size gene can be positioned as the rightmost gene. By using one of the genes to identify the number of expressed genes in a chromosome, it is possible for each chromosome to in general have a different number of expressed genes. Moreover, since the expressed sub-set-size gene is a gene of the chromosome, it can be subjected to genetic evolutionary operations similarly to the other genes of the chromosome so as to optimize the number of expressed genes in the chromosome. This ability to evolve the number of genes is advantageous because typically the optimal number of genes for a particular medical diagnostic test is not known a priori.

With reference to FIGS. 4A, 4B, 4C, and 4D, suitable approaches for generating offspring chromosomes and for updating each new generation of the chromosome population 12 are described. In the illustrated embodiments, the genetic algorithm 10 implements a version of the Eshelman CHC genetic algorithm which is modified to accommodate the variable number of expressed genes in each chromosome set forth by the expressed sub-set-size gene 80 of that chromosome. These modifications include modifying the crossover operator 20 to propagate the expressed sub-set-size gene 80, which is different in kind from the remaining genes, into offspring chromosomes. The crossover operator 20 is also modified to promote expression and propagation of genes of the offspring which are common to the parent chromosomes. For example, the in some embodiments common genes are not mutated, and in some embodiments the positions of the common genes are biased toward the expressed sub-set-size gene 80, that is, are biased toward the portion of the chromosome which is expressed. Additionally, the Eshelman CHC genetic algorithm is modified with respect to the selection algorithm 40 to use a selection criterion biased toward selecting chromosomes having a smaller number of expressed genes over chromosomes having a larger number of expressed genes. Thus, the evolutionary drive is toward a small number of expressed genes.

While modified Eshelman CHC algorithms are described and illustrated for expository purposes, it is to be appreciated that other genetic algorithms can be similarly adapted to employ the disclosed variable number of expressed genes in each chromosome, the biasing toward expression and propagation of common genes, the biasing toward smaller number of genes, and so forth.

Figure 4A:
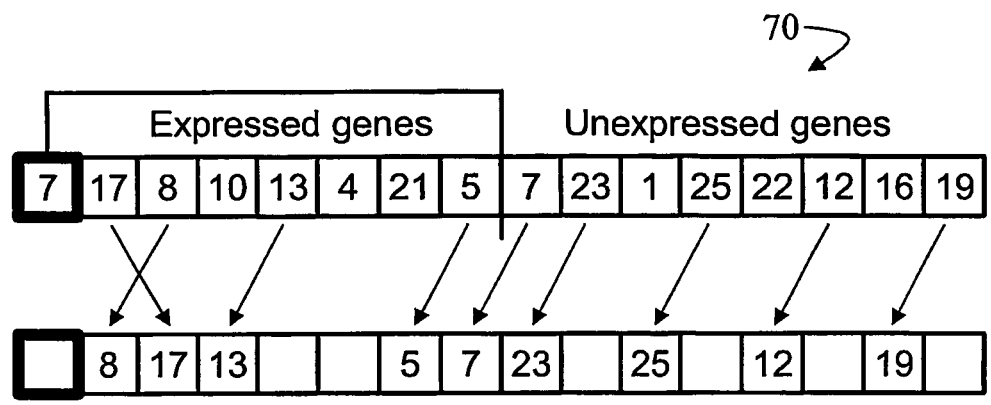
Figure 4B:
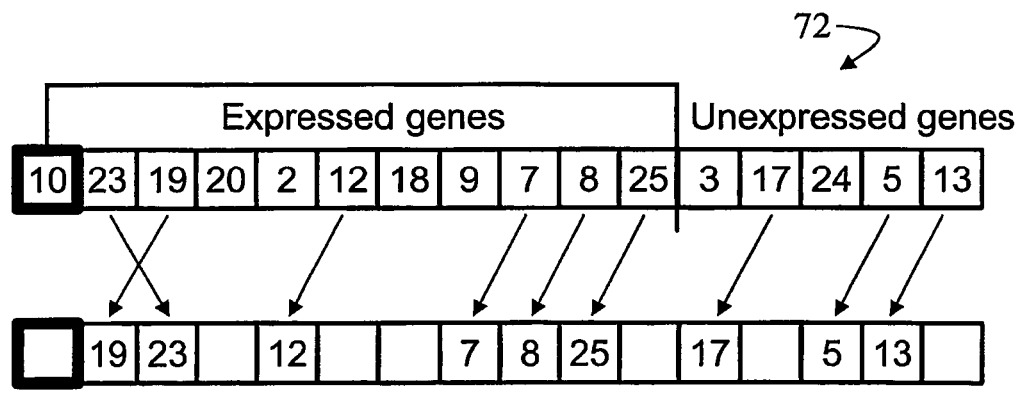

With reference to FIGS. 4A and 4B, selected parents are combined to produce offspring chromosomes. In the Eshelman CHC algorithm, each offspring chromosome is derived from two parent chromosomes, and typically each pair of parent chromosomes is used to produce two offspring chromosomes. Other crossover combinations can be used, however. For expository purposes, the chromosomes 70, 72 of FIGS. 3A and 3B, respectively, are paired as parent chromosomes to generate two offspring chromosomes. In producing the offspring, the common gene values of the parent chromosomes 70, 72 are copied into the offspring chromosome. For parent chromosomes 70, 72, the set of common gene values is: {5, 7, 8, 12, 13, 17, 19, 23, 25}. In FIG. 4A, a first offspring chromosome receives the common gene values in the order they are present in the first parent chromosome 70, while in FIG. 4B a second offspring chromosome receives the common gene values in the order they are present in the second parent chromosome 72.

In some embodiments, the common gene values are copied into the corresponding positions in the offspring chromosome as in the parent chromosome, but with a biasing toward the expressed gene positions. In the illustrated embodiment, this biasing is achieved as shown in FIGS. 4A and 4B by shifting each common gene value one position to the left, that is, one position toward the expressed sub-set gene 80 of the chromosome. Since the expressed genes are immediately to the right of the expressed sub-set-size gene 80, this left-shift has the effect of biasing the common gene values toward being expressed.

Additionally, at least occasionally the ordering of the common gene values in the offspring chromosome is optionally varied from the ordering of the common gene values in the parent chromosome. In the illustrated embodiment, this biasing is achieved as shown in FIGS. 4A and 4B by performing a swap of gene values in the case where two or more of the left-most gene values of the parent chromosome are common gene values. For example, in FIG. 4A the two leftmost gene values 17, 8 of the first parent chromosome 70 are common gene values, and so they are copied in the reverse order 8, 17 in the first offspring chromosome. Similarly, the two common gene values 23, 19 in the second parent chromosome 72 are copied in the reverse order 19, 23 in the second offspring chromosome. More generally, if a contiguous three or more of the leftmost gene values of the parent chromosome are common genes, then they are left-rotated with the leftmost gene value of the parent chromosome being copied over at the rightmost end of the contiguous sequence of three or more common gene values.

The approach for varying the ordering of the common gene values illustrated in FIGS. 4A and 4B is an example. As the chromosome population 12 evolves with the biasing of common gene values toward the left, there is a tendency for the common gene values to pile up at the left-hand side of the ordered sequence of genes. The common gene values therefore tend to be expressed. The varying of the ordering tends to produce mixing that promotes evolutionary variation, and prevents the left-most common gene value from always being expressed in every offspring chromosome.

Figure 4C:
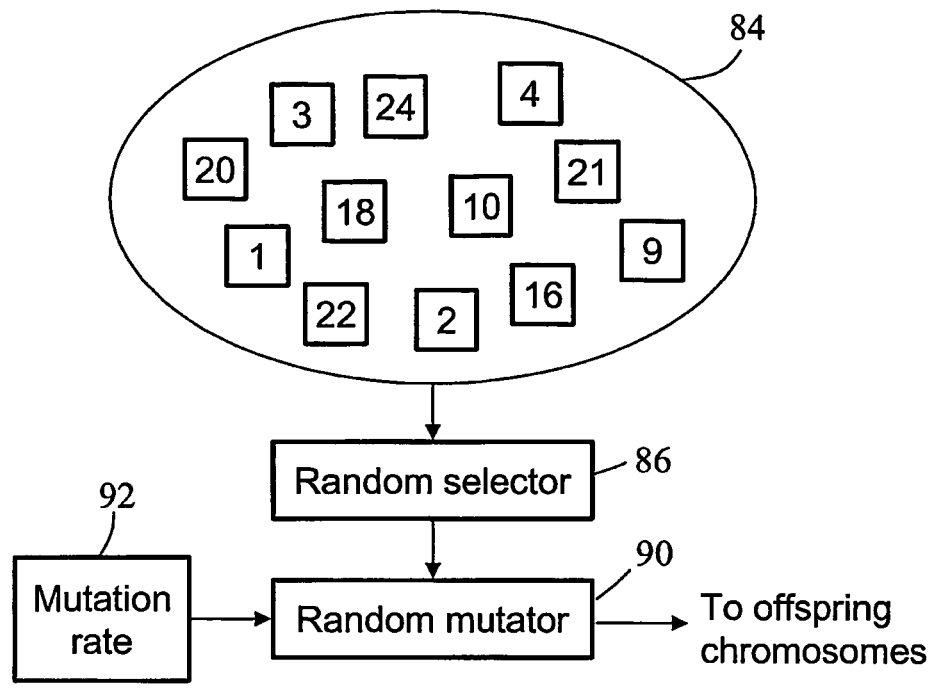

With continuing reference to FIGS. 4A and 4B and with further reference to FIG. 4C, those genes of the offspring chromosomes which are not filled by common gene values are filled with gene values that are unique to one or the other of the parent chromosomes 70, 72. The example parent chromosomes 70, 72 define an example set of unique gene values 84 including twelve unique gene values: {1, 2, 3, 4, 9, 10, 16, 18, 20, 21, 22, 24}. A random selector 86 selects one of the unique gene values to fill each gene of the offspring chromosome that remains after the common gene values are used up.

A random mutator 90 selectively mutates the unique gene values on a random or pseudorandom basis. In the illustrated embodiment, only the unique gene values that are applied to filling genes of the offspring chromosomes undergo selective mutation. The common gene values are not mutated. By not mutating the common gene values, propagation of common gene values across generations is promoted. The common gene values are in general expected to tend to be more likely to confer fitness than unique gene values.

Not mutating the common gene values also promotes convergence of the computational genetic evolving toward optimal chromosomes. Because the common gene values are not mutated, a chromosome configuration that is relatively stable across generations is more readily achieved. This, in turn, allows a mutation rate 92 of the unique gene values to be relatively larger than would be the case if all gene values including the common gene values are selectively mutated. In some embodiments, a mutation rate for the unique gene values of greater than 5% has been found to be suitable. In some embodiments, a mutation rate for the unique gene values of around 15% has been found to be suitable. By contrast, when both common and unique gene values are mutated selectively, mutation rates greater than 5% generally leads to poor convergence characteristics for the genetic evolving.

In FIG. 4C, randomly selected unique gene values are used to fill those genes of the offspring chromosome that are not filled with common gene values. However, other approaches can be employed. For example, the unique gene values of the two parent chromosomes 70, 72 can be paired up, left-to-right, and half randomly chosen for swapping between the offspring. Thus, the genes of the offspring chromosome of FIG. 4A in this approach would receive the values {10, 4, 21, 1, 22, and 16} from parent chromosome 70 while the offspring chromosome of FIG. 4B would receive the values {20, 2, 18, 9, 3, and 24} from parent chromosome 72. However, one-half of those unique gene values would be randomly pairwise-swapped between the offspring. Hence, for example, the third ordinal position gene values 21, 18, the fifth ordinal position gene values 22, 3, and the sixth ordinal position gene values 16, 24 may be randomly swapped between the two offspring. The random mutator 90 also would operate on the unique gene values as previously described.

Figure 4D:
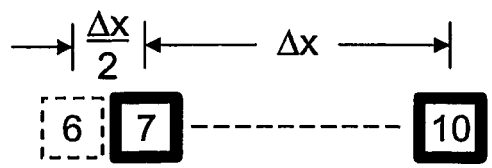

With reference to FIG. 4D, the Eshelman CHC genetic algorithm is further modified to produce a suitable value of the expressed sub-set-size gene 80 for the offspring chromosomes. The values of the expressed sub-set-size gene 80 of the example parent chromosomes 70, 72 are 7 and 10, respectively. Thus, the value of the expressed sub-set-size gene 80 of the offspring chromosomes should lie between 7 and 10 inclusive. Optionally, this range is extended to increase the effectiveness of the genetic evolution in reaching chromosomes with larger or smaller numbers of expressed genes. In the illustrated embodiment, the range is increased by one-half of a range $\Delta x$ between the values of the expressed sub-set-size gene 80 of the two parent chromosomes 70, 72. This extension value is truncated to define an integer, and is applied in the direction of the value of the expressed sub-set-size gene 80 of the more fit parent. In FIG. 4D, it is assumed that the parent chromosome 70 having a value of 7 for the expressed sub-set-size gene 80 is more fit than the parent chromosome 72 that has a value of 10 for the expressed sub-set-size gene 80. The range is therefore extended by $\Delta x/2 = \text{INT}[(10-7)/2] = \text{INT}[1.5] = 1$ below the lower value of 7 such that the values of the expressed sub-set-size gene 80 of the parent chromosomes 70, 72 define a range of [6,10] inclusive. The value of the expressed sub-set-size gene 80 of each offspring chromosome is randomly or pseudorandomly selected from the range [6,10]. If the parent chromosome 72 had been more fit than the parent chromosome 70, then the extension would have been above the value 10 of the expressed sub-set-size gene 80 of the chromosome 72, thus defining a range of [7,11] for selection. Moreover, if the extension would go beyond a selected bound (for example, larger than the number of genes in the chromosome, or less than one, or less than a selected minimum number of expressed genes) then the range for the offspring chromosome expressed sub-set-size gene value is suitably truncated.

With returning reference to FIG. 1, the selection algorithm 40 of the genetic algorithm 10 is modified versus the Eshelman CHC algorithm to be biased to favor chromosomes having a smaller number of expressed genes. A smaller number of expressed genes corresponds to a smaller sub-set of measurements 52 in the diagnostic test 50, and reduces the likelihood of overfitting the learning cases 22. In some embodiments, a hierarchical selection is used for comparing two chromosomes. One such selection is set forth by the following pseudocode:

```
if (classification_errors(Offspring) < classification_errors(Parent))
        then replace Parent with Offspring
if ( (classification_errors(Offspring) = classification_errors(Parent))
        and (sss(Offspring) < sss(Parent)) )                    (2),
        then replace Parent with Offspring
if ( (classification_errors(Offspring) = classification_errors(Parent))
        and (sss(Offspring) = sss(Parent)) )
        then randomly choose whether to replace Parent with Offspring
``` where in the Pseudocode (2): classification_errors( ) is the fitness measure of each chromosome determined by the classifier testing algorithm 32 and measures the number of classification errors produced by that chromosome with its optimized classifier function; and sss( ) is the value of the expressed sub-set-size gene 80. The Pseudocode (2) is suitably applied as follows: (i) the chromosomes of the parent chromosome population are ranked by fitness; (ii) the offspring chromosomes are ranked by fitness; (iii) the most fit offspring chromosome and the least fit parent chromosome are compared using the Pseudocode (2) and if appropriate the Parent chromosome is replaced by the Offspring chromosome in the chromosome population; and (iv) the operation (iii) is repeated until the Parent is not replaced by the Offspring (thus implying that none of the remaining Offspring are as fit as the least fit Parent).

In selecting the parent chromosomes for producing offspring, the Eshelman CHC incest prevention mechanism is optionally employed. Incest prevention keeps crossover from being performed between parents that are too similar. Typically, incest prevention is determined with respect to the expressed genes of the parent chromosome. However, since the value of the expressed sub-set-size gene 80 in the offspring chromosome may be larger than one or both values of the expressed sub-set-size gene 80 in the parent chromosomes, incest prevention for two potential parent chromosomes is suitably determined with respect to the maximum value of the expressed sub-set-size gene 80 that an offspring chromosome of such a pairing could acquire. Other features of the Eshelman CHC genetic algorithm are also optionally incorporated, such as providing for soft restarts to work against premature convergence.

With reference to FIG. 5, the effectiveness of using the expressed sub-set-size gene 80 along with biasing toward smaller numbers of expressed genes is illustrated. FIG. 5 shows a scatter plot with the value of the expressed sub-set-size gene 80 of each chromosome plotted along the ordinate (y-axis) and the trial number (corresponding to time) plotted along the abscissa (x-axis). The number of genes per chromosome was set to thirty for the run illustrated in FIG. 5, and the chromosome population 12 included 100 chromosomes. The initial chromosome population had values of the expressed sub-set-size gene 80 randomly selected between 1 and 30. In an initial region 100 early on in the genetic evolution, the chromosomes with small values of the expressed sub-set-size gene 80 (for example, less than about 10-12) died out. Since the values of the genes were random in the initial chromosome population, the chances that a good gene or two are present in a given chromosome is higher for those chromosomes with large values of the expressed sub-set-size gene 80 than those with small values of the expressed sub-set-size gene 80. Hence, the chromosomes with small values die out in the initial region 100. However, after some 1,000 trials, chromosomes with values of the expressed sub-set-size gene 80 less than ten begin to reappear. The values of the genes were no longer random after 1,000 trials, but have begun to be inherited from parents who survived the previous generations. Then, at about 40,000-50,000 trials, chromosomes with very large values of the expressed sub-set-size gene 80 began to die out. The chromosomes of the chromosome population 12 after 40,000-50,000 trials were achieving similar accuracies, and so the selection pressure for small values of the expressed sub-set-size gene 80 was beginning to take effect. The average value of the expressed sub-set-size gene 80 rapidly declined beyond 50,000 trials, and decreased until most of the chromosome population 12 had values of the expressed sub-set-size gene 80 of three or four. At a point just before 100,000 trials, the modified Eshelman CHC genetic algorithm triggered a soft restart because the population had converged. At the soft restart, the whole range of values of the expressed sub-set-size gene 80 between 1 and 30 inclusive was re-introduced. The course of evolution continues then beyond the edge of FIG. 5 where a similar dynamics were seen again (not shown in FIG. 5).

With returning reference to FIG. 1, each classifier is trained using the training cases 26 which is a sub-set of the learning cases 22. After training, the classifier is tested on the test cases 28 which is another sub-set of the learning cases 22. The cross-validation and noise-adding algorithm 24 re-divides the learning cases 22 into training cases 26 and test cases 28 before each new generation of the chromosome population 12 is processed. Those parent chromosomes which survive from the previous generation are re-evaluated along with their offspring chromosomes using a different segmentation of the learning cases 22 into training cases 26 and test cases 28. Thus, for a chromosome to propagate over several generations and thus spread its genes in the chromosome population 12, it must consistently perform better than average, and consistent performance requires good generalization from many different randomly selected training sets 26. The segmentation of the learning cases 22 into training cases 26 and test cases 28 is known as cross-validation. Various cross-validation approaches can be used, such as leave-out cross-validation, k-fold cross-validation, and so forth.

With continuing reference to FIG. 1, in some embodiments the cross-validation and noise-adding algorithm 24 introduces a selected level of simulated noise into values of the set of measurements of the measured test subjects as the learning cases 22 are divided into training cases 26 and test cases 28. The introduction of simulated noise counteracts possible fitting of the classification functions to correlations of measurement errors. For example, if the measuring instruments systematically read slightly high when the cancer cases were measured and slightly low for the cancer-free cases, the genetic evolving may converge onto these systematic error patterns. The optional introduction of simulated noise by the cross-validation and noise-adding algorithm 24 perturbs the measurements for each generation of the evolutionary search. In one approach, Gaussian simulated noise is added according to:

$$x' = x + (\text{gauss}(\ ) \cdot x \cdot cv) \quad (3),$$

where x is the measurement value, x' is the measurement value with simulated noise added, cv is the coefficient of variation (that is, the standard deviation divided by the mean, x), and gauss( ) is a Gaussian function with zero mean and unit variance. This introduction of simulated noise is performed during the dividing of the learning cases 22 into training and test cases 26, 28 performed before each successive generation of the chromosome population 12 is processed.

Introducing simulated noise reduces sensitivity of the genetic evolving to systematic measurement errors, but diminishes the tendency for the discovery algorithm to find weak patterns. For some bioinformatics measurement sets, it has been found that coefficients of variation (cv) greater than about 2% in the added simulated Gaussian noise prevents convergence to weak biologically significant patterns.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A method for optimizing medical diagnostic classifiers using a genetic algorithm, the method comprising:
   training a classifier via a set of learning cases, the learning cases comprising measurement data for a set of measurements acquired from a pool of human test subjects some of whom have cancer and some of whom do not have cancer, the measurement data comprising measured concentrations of organic macromolecules;
   producing a first generation chromosome population comprising chromosomes, each chromosome represented as chromosomal bit-strings;
   assigning an index value to each gene of an ordered set of genes, wherein each index indexes a measurement of the set of measurements, and each gene of the ordered set of genes is represented as genetic bit-strings;
   assigning an ordinal position value to an expressed sub-set-size gene that separates expressed genes from unexpressed genes in the ordered set of genes;
   generating a fitness criterion that qualifies effectiveness of the expressed genes of each chromosome for identifying the cancer in the set of learning cases, the fitness criterion being evaluated without reference to the unexpressed genes of the chromosome to produce successive generation chromosome populations, wherein computational genetic evolving is performed by a computing system, the computational genetic evolving including:
      mating pairs of parent chromosomes of the present generation chromosome population to generate offspring chromosomes,
      for each offspring chromosome, computing a value for the fitness criterion using a classifier defined by the measurements specified by the expressed genes of the offspring chromosome without reference to the unexpressed genes of the offspring chromosome and trained on the set of learning cases, and
      selecting the next generation chromosome population based on the computed values of the fitness criterion; and
   selecting a classifier corresponding to a most it chromosome identified by genetic evolving.

2. The method as set forth in claim 1, wherein the ordered set of genes has first and second ends with the gene closest to the first end being an expressed gene, and the genetic evolving includes:
   generating each offspring chromosome from two parent chromosomes of the present generation chromosome population by: (i) filling genes of the offspring chromosome with gene values common to both parent chromosomes using the ordering of the common gene values in a selected one of the two parent chromosomes and biasing the filling toward the first end of the ordered set of genes of the offspring chromosome and (ii) filling remaining genes with gene values that are unique to one or other of the parent chromosomes.

3. The method as set forth in claim 2, wherein the filling of genes with gene values common to both parent chromosomes includes:
   varying the ordering of the common gene values in the offspring chromosome from the ordering of the common gene values in the selected one of the two parent chromosomes.

4. The method as set forth in claim 1, wherein the computational genetic evolving includes:
   replacing a selected chromosome of the present generation chromosome population with a selected offspring chromosome if either: (i) the selected offspring chromosome is more fit than the selected chromosome of the present generation chromosome population, or (ii) the selected offspring chromosome is as fit as the selected chromosome of the present generation chromosome population and the selected offspring chromosome has fewer expressed genes than the selected chromosome of the present generation chromosome population.

5. The method as set forth in claim 4, wherein:
   the selected offspring chromosome is the most fit offspring chromosome and the selected chromosome of the present generation chromosome population is the least fit chromosome of the present generation chromosome population; and
   the replacing is repeated until the most fit offspring chromosome is less fit than the least fit chromosome of the present generation chromosome population.

6. The method as set forth in claim 1, wherein the method further includes:
   before producing each successive generation chromosome population, introducing a selected level of simulated noise into values of the measurements of the learning cases.

7. A method for classifying whether a medical subject has cancer using a classifier optimized using a genetic algorithm, the method comprising:
   generating a medical diagnostic classifier by performing a method including:
      training the classifier via a set of learning cases, the learning cases comprising measurement data for a set of measurements acquired from a pool of human test subjects some of whom have cancer and some of whom do not have cancer, the measurement data characterizing concentrations of organic macromolecules in the human test subjects;
      producing a first generation chromosome population comprising chromosomes, each chromosome represented as chromosomal bit-strings;
      assigning an index value to each gene of an ordered set of genes, wherein each index indexes a measurement of the set of measurements, and each gene of the ordered set of genes is represented as generic bit-strings;
      assigning an ordinal position value to an expressed sub-set-size gene that separates expressed genes from unexpressed genes in the ordered set of genes;
      generating a fitness criterion that quantifies effectiveness of the expressed genes of each chromosome for classifying the human test subjects into either a positive group having cancer or a negative group not having cancer, the fitness criterion being evaluated without reference to the unexpressed genes of the chromosome to produce successive generation chromosome populations, wherein computational genetic evolving is performed by a computing system, the computational genetic evolving including:

mating pairs of parent chromosomes of the present generation chromosome population to generate offspring chromosomes, for each offspring chromosome, computing a value for the fitness criterion using a classifier defined by the measurements specified by the expressed genes of the offspring chromosome without reference to the unexpressed genes of the offspring chromosome and trained on the set of learning cases, and selecting the next generation chromosome population based on the computed values of the fitness criterion; and selecting a classifier corresponding to a most fit chromosome;

wherein the classifier corresponding to a most fit chromosome is selected as the medical diagnostic classifier; and classifying measurement data for the set of measurements acquired from the medical subject using the medical diagnostic classifier implemented by a computer to classify the medical subject as to whether the medical subject has cancer.

8. The method as set forth in claim 7, wherein the set of measurements characterizing concentrations of organic macromolecules in a medical subject is one of:

a set of measurements of dots of a microarray processed using a biological sample taken from the medical subject, and a set of signal levels of a mass spectrogram measured for a biological sample taken from the medical subject.

9. A method for optimizing medical diagnostic classifiers using a genetic algorithm, the method comprising:

training a classifier via a set of learning cases, the learning cases comprising measurement data for a set of measurements acquired from a pool of human test subjects some of whom have cancer and some of whom do not have cancer, the measurement data comprising measured concentrations of organic macromolecules;

producing a first generation chromosome population of chromosomes, each chromosome represented as chromosomal bit-strings;

generating successive generation chromosome populations by:

generating offspring chromosomes from parent chromosomes of the present chromosome population by: (i) filling genes of the offspring chromosome with gene values common to both parent chromosomes and (ii) filling remaining genes with gene values that are unique to one or the other of the parent chromosomes, selectively mutating genes values of the offspring chromosomes that are unique to one or the other of the parent chromosomes without mutating gene values of the offspring chromosomes that are common to both parent chromosomes, after the selective mutating, training a classifier for each offspring chromosome that uses a sub-set of the set of measurements, generating a fitness criterion that quantifies effectiveness of the classifier for identifying cancer in the set of learning cases, and updating the chromosome population with offspring chromosomes based on a fitness of each chromosome determined using the trained classifier of that chromosome and measured by the fitness criterion; and selecting the trained classifier corresponding to a most fit chromosome.

10. The method as set forth in claim 9, wherein a mutation rate for the selective mutating of the gene values that are unique to one or the other of the parent chromosomes is greater than 5%.

11. The method as set forth in claim 9, wherein only a sub-set of the genes of each chromosome are expressed genes and the classifier is trained using the sub-set of the associated measurements specified by the expressed genes of that chromosome.

12. A method for classifying whether a medical subject has cancer, the method comprising:

generating a medical diagnostic classifier by performing a method including:

training a classifier via a set of learning cases, the learning cases comprising measurement data for a set of measurements acquired from a pool of human test subjects some of whom have cancer and some of whom do not have cancer, the measurement data comprising measured concentrations of organic macromolecules;

producing a first generation chromosome population of chromosomes, each chromosome represented as chromosomal bit-strings;

generating successive generation chromosome populations by:

generating offspring chromosomes from patent chromosomes of the present chromosome population by: (i) filling genes of the offspring chromosome with gene values common to both parent chromosomes and (ii) filling remaining genes with gene values that are unique to one or the other of the parent chromosomes, selectively mutating genes values of the offspring chromosomes that are unique to one or the other of the parent chromosomes without mutating gene values of the offspring chromosomes that are common to both parent chromosomes, after the selective mutating, training a classifier for each offspring chromosome that uses a sub-set of the set of measurements, generating a fitness criterion that quantifies effectiveness of the classifier for identifying cancer in the set of learning cases, and updating the chromosome population with offspring chromosomes based on a fitness of each chromosome determined using the trained classifier of that chromosome and measured by the fitness criterion; and selecting the trained classifier corresponding to a most fit chromosome, wherein the trained classifier corresponding to a most fit chromosome is selected as the medical diagnostic classifier; and classifying measurement data for the set of measurements acquired from the medical subject using the medical diagnostic classifier implemented by a computer to classify the medical subject as to whether the medical subject has cancer.

13. A method for optimizing medical diagnostic classifiers using a genetic algorithm, the method comprising:

training a classifier via a set of learning cases, the learning cases comprising measurement data for a set of measurements acquired from a pool of human test subjects some of whom have cancer and some of whom do not have cancer, the measurement data comprising measured concentrations of organic macromolecules;

producing a first generation chromosome population of chromosomes, each chromosome represented as chromosomal bit-strings;

generating successive generation chromosome populations by:

introducing a selected level of simulated noise into the measurement data for the set of measurements acquired from the pool of human subjects, generating offspring chromosomes by mating chromosomes of the present chromosome population, selectively mutating genes of the offspring chromosomes, after the selective mutating, training a classifier for each offspring chromosome that uses a sub-set of the set of measurements, generating a fitness criterion that quantifies effectiveness of the classifier for identifying cancer in the set of learning cases with the introduced simulated noise, and updating the chromosome population with offspring chromosomes based on a fitness of each chromosome determined using the trained classifier of that chromosome and measured by the fitness criterion respective to the measurement data for the set of measurements acquired from the pool of human subjects with the introduced simulated noise; and selecting the trained classifier corresponding to a most fit chromosome;

wherein the selecting is performed by a computing system.

14. A method for classifying whether a medical subject has cancer using a classifier optimized using a genetic algorithm, the method comprising:

generating a medical diagnostic classifier by performing a method including:

training a classifier via a set of learning cases, the learning cases comprising measurement data for a set of measurements acquired from a pool of human test subjects some of whom have cancer and some of whom do not have cancer, the measurement data comprising measured concentrations of organic macromolecules;

producing a first generation chromosome population of chromosomes, each chromosome represented as chromosomal bit-strings;

generating successive generation chromosome populations by:

introducing a selected level of simulated noise into the measurement data for the set of measurements acquired from the pool of human subjects, generating offspring chromosomes by mating chromosomes of the present chromosome population, selectively mutating genes of the offspring chromosomes, after the selective mutating, training a classifier for each offspring chromosome that uses a sub-set of the associated set of measurements, generating a fitness criterion that quantifies effectiveness or the classifier for identifying cancer in the set of learning cases with the introduced simulated noise, and updating the chromosome population with offspring chromosomes based on a fitness of each chromosome determined using the trained classifier of that chromosome and measured by the fitness criterion respective to the measurement data for the set of measurements acquired from the pool of human subjects with the introduced simulated noise; and selecting the trained classifier corresponding to a most fit chromosome;

wherein the selecting is performed by a computing system and wherein the trained classifier corresponding to a most fit chromosome is selected as the medical diagnostic classifier; and classifying measurement data for the set of measurements acquired from the medical subject using the medical diagnostic classifier implemented by a computer, to classify the medical subject as to whether the medical subject has cancer.

15. A method for optimizing medical diagnostic classifiers using a genetic algorithm, the method comprising:

training a classifier via a set of learning cases, the learning cases comprising measurement data for a set of measurements acquired from a pool of human test subjects some of whom have cancer and some of whom do not have cancer, the measurement data comprising measured concentrations of organic macromolecules;

producing a first generating chromosome population comprising chromosomes, each chromosome represented as bit-strings;

assigning an index value to each gene of an ordered set of genes, wherein each index indexes a measurement of the set of measurements, and each gene of the ordered set of genes is represented as generic bit-strings;

wherein the producing step includes:

assigning an ordinal position value to a number of expressed genes;

generating a fitness criterion quantifying effectiveness of the expressed genes of each chromosome for identifying cancer in the set of learning cases, the fitness criterion being evaluated without reference to unexpressed genes of each chromosome, and selecting chromosomes that survive into each successive generation using a selection criterion biased toward selecting chromosomes having a smaller number of expressed genes over chromosomes having a larger number of expressed genes; and selecting a most fit chromosome as measured by the fitness criterion;

wherein the selecting is performed by a computing system.

16. The method as set forth in claim 15, wherein the genetic evolving includes:

generating an offspring chromosome by mating two selected parent chromosomes of the present chromosome population; and selectively mutating genes of the offspring chromosome that are unique to one or the other of the two parent chromosomes without mutating genes of the offspring chromosome that are common to both parent chromosomes.

17. The method as set forth in claim 15, wherein the genetic evolving includes:

generating offspring chromosomes by mating selected parent chromosomes of the parent chromosome population and introducing a select level of simulated noise into measurement values associated with the parent chromosomes.

* * * * *